(12) United States Patent
Loach

(10) Patent No.: US 12,186,078 B2
(45) Date of Patent: Jan. 7, 2025

(54) APPARATUS FOR COUPLING RADIATION INTO AND OUT OF AN OPTICAL FIBER

(71) Applicant: NGPod Global Limited, Manchester (GB)

(72) Inventor: Andrew Loach, Wirral (GB)

(*) Notice: Subject to any disclaimer, the term of this patent is extended or adjusted under 35 U.S.C. 154(b) by 667 days.

(21) Appl. No.: 17/416,596

(22) PCT Filed: Dec. 20, 2019

(86) PCT No.: PCT/GB2019/053671
§ 371 (c)(1),
(2) Date: Jun. 21, 2021

(87) PCT Pub. No.: WO2020/128519
PCT Pub. Date: Jun. 25, 2020

(65) Prior Publication Data
US 2022/0054052 A1   Feb. 24, 2022

(30) Foreign Application Priority Data
Dec. 21, 2018 (GB) .................................. 1821081

(51) Int. Cl.
*A61B 5/1459* (2006.01)
*A61B 5/145* (2006.01)
*G01N 21/77* (2006.01)
*G02B 6/42* (2006.01)
*A61J 15/00* (2006.01)
*G01N 21/80* (2006.01)

(52) U.S. Cl.
CPC ........ *A61B 5/1459* (2013.01); *A61B 5/14539* (2013.01); *A61B 5/14546* (2013.01); *G01N 21/7703* (2013.01); *G02B 6/4246* (2013.01); *A61J 15/008* (2015.05); *A61J 15/0084* (2015.05); *G01N 21/80* (2013.01); *G02B 6/4298* (2013.01)

(58) Field of Classification Search
CPC .............. A61B 5/14539; A61B 5/1459; G01N 21/7703; G01N 21/80; G02B 6/32
See application file for complete search history.

(56) References Cited

U.S. PATENT DOCUMENTS

| 3,474,252 A | 10/1969 | Jacobsen |
| 4,292,512 A * | 9/1981 | Miller ............... H01L 31/02327 257/E31.128 |

(Continued)

FOREIGN PATENT DOCUMENTS

CN    1079302 A  * 12/1993

*Primary Examiner* — Michael Stahl
(74) *Attorney, Agent, or Firm* — Edwin D. Schindler

(57) ABSTRACT

An apparatus for coupling radiation into and out of an optical fiber includes an optical element, a radiation system and a sensor system. The optical element is for coupling radiation into and out of the optical fiber. The radiation system produces input radiation, so that the input radiation is at least partially received by the optical element. The sensor system is for receiving output radiation from the optical element and operates to generate a signal indicative of at least one characteristic of the output radiation. The optical element, the radiation system and the sensor system are generally co-axial and the radiation system and the sensor system are both disposed on the same side of the optical element.

11 Claims, 6 Drawing Sheets

(56) References Cited

U.S. PATENT DOCUMENTS

| | | | | |
|---|---|---|---|---|
| 4,773,722 A | * | 9/1988 | Perino | H01L 31/0232 |
| | | | | 398/139 |
| 5,037,615 A | * | 8/1991 | Kane | G01N 21/7703 |
| | | | | 422/82.07 |
| 5,085,216 A | * | 2/1992 | Henley, Jr. | A61B 5/14503 |
| | | | | 600/593 |
| 5,277,872 A | * | 1/1994 | Bankert | G01N 31/221 |
| | | | | 422/82.07 |
| 5,787,215 A | * | 7/1998 | Kuhara | H01L 31/12 |
| | | | | 398/79 |
| 6,136,611 A | * | 10/2000 | Saaski | G02B 6/4204 |
| | | | | 436/805 |
| 7,058,309 B1 | * | 6/2006 | Eisenberger | G02B 6/4246 |
| | | | | 398/41 |
| 2005/0041207 A1 | | 2/2005 | Miller et al. | |
| 2006/0257072 A1 | * | 11/2006 | Harres | G02B 6/4246 |
| | | | | 385/33 |
| 2007/0036493 A1 | * | 2/2007 | Brenner | G02B 6/4246 |
| | | | | 385/89 |
| 2009/0275825 A1 | * | 11/2009 | Thomas | G01N 21/78 |
| | | | | 604/264 |
| 2015/0157194 A1 | | 6/2015 | Okuda et al. | |
| 2017/0239149 A1 | | 8/2017 | Small et al. | |

\* cited by examiner

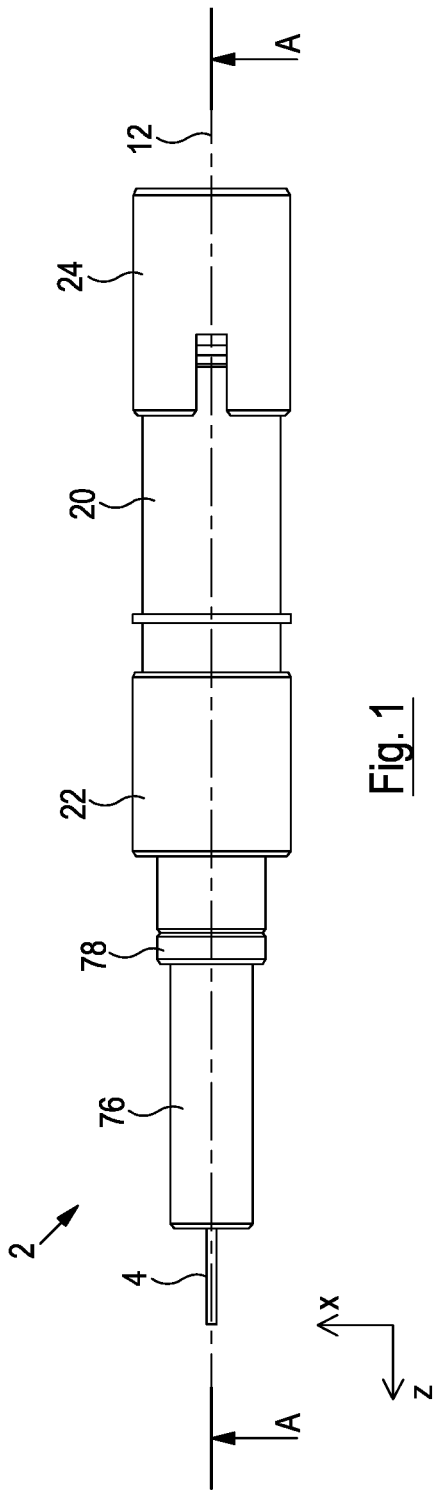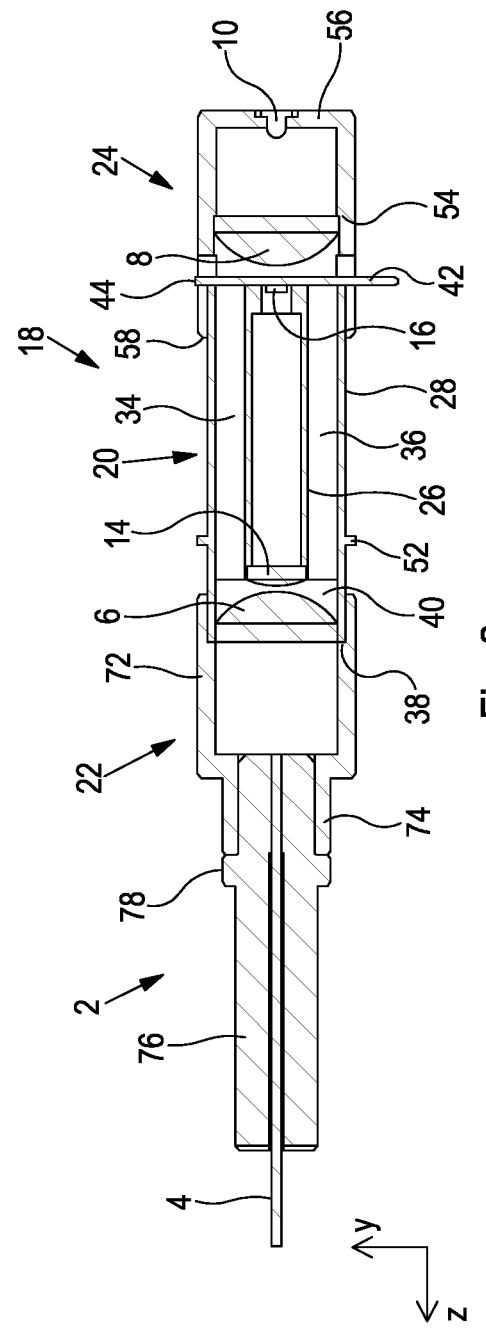

SECTION A-A

A-A

APPARATUS FOR COUPLING RADIATION INTO AND OUT OF AN OPTICAL FIBER

The present invention relates to an apparatus for coupling radiation into and out of an optical fiber. In particular, it may relate to an apparatus that is operable to couple radiation into one end of an optical fiber and to receive radiation that has reflected from an opposite end of the optical fiber such that a characteristic of the reflected radiation (for example its colour) can be determined.

Such an apparatus may find application in the field of medical tubes, such as, for example, nasogastric and nasointestinal feeding tubes, and particularly in the confirmation of correct placement and/or avoidance of misplacement of the portion of the tube through which the fluid exits.

Human or animal patients can sometimes be incapable of feeding themselves by conventional means. In such circumstances it is desirable to deliver nutrients into the stomach or small intestine by way of a feeding tube. This is generally carried out by passing a tube through the nasal passage of the patient and into the stomach or the small intestine by way of the gastrointestinal tract. The distal end of such feeding tubes comprises one or more fluid output apertures, which act to deliver fluid nutrients to predetermined locations such as, for example, the stomach or small intestine. Correct positioning of the fluid output apertures within the stomach or small intestine can be essential for the safety of the patient. For example, misdirection of the feeding tube upon insertion via the nasal cavity such that the leading end of the feeding tube is directed towards the lungs may occur, particularly with patients who have an inhibited cough or gag reflex such as, for example, the critically ill and premature babies. Such misplacement of the fluid output apertures may, upon feeding, lead to serious pleuropulmonary complications such as, for example, pneumonia, abscess and empyema.

Also, in certain circumstances it may be desirable for certain fluid nutrients to be delivered to specific parts of the digestive system such as, for example, specifically to the stomach and/or specifically to the small intestine. Again, correct placement of the fluid outlet apertures can be essential.

One known system for determining whether or not the fluid outlet apertures are disposed in a correct position is disclosed in patent document number EP2412311A2. This describes a feeding tube positioning means that has an optical waveguide and a colour-change indicator (for example a pH indicator or a carbon dioxide indicator) at a distal end of the optical waveguide. The optical waveguide is dimensioned to be insertable into the lumen of a feeding tube. In use, the optical waveguide carries input light to the sensor means. A portion of the input light is reflected from the sensor means as output light, the colour of the output light being indicative of the position of the feeding tube. The output light is carried to the proximate end of the position confirmation device, by the output optical waveguide, at which it is viewed by the user to determine the position of the tube in the human or animal body.

It may be desirable to provide an alternative apparatus for coupling radiation into and out of an optical fiber which at least partially addresses one or more of the problems of the prior art, whether identified herein or elsewhere. Such an apparatus may form part of a feeding tube placement measurement system.

According to a first aspect of the invention there is a provided an apparatus for coupling radiation into and out of an optical fiber, the apparatus comprising: an optical element for coupling radiation into and out of the optical fiber; a radiation system operable to produce input radiation, the radiation system arranged such that the input radiation is at least partially received by the optical element; and a sensor system for receiving output radiation from the optical element and operable to generate a signal indicative of at least one characteristic of the output radiation; wherein the optical element, the radiation system and the sensor system are generally co-axial and the radiation system and the sensor system are both disposed on the same side of the optical element.

The apparatus according to the first aspect of the invention provides an arrangement that is operable to couple radiation into and out of an optical fiber. The apparatus may, for example, find application in determining a property of a remote location. The radiation system can couple the input radiation into an optical fiber, via the optical element. The radiation can propagate along the optical element to a remote location. At least a portion of the radiation can scatter from a distal end of the optical fiber and propagate back along the optical element to the apparatus, where it can be at least partial received and analyzed by the sensor system (via the optical element). For example, in one application the distal end of the optical fiber may comprise an indicator material, the colour of which is indicative of a property of a remote location. For example, the colour of the indicator material may be indicative of the pH value of the remote location. In use, the optical fiber may be inserted in a feeding tube so that a medical professional can determine that it has been placed correctly before the feeding tube is used to provide food to a patient.

It will be appreciated that, in general, radiation may enter and/or leave an optical fiber at a range of different angles to an optical axis of the optical fiber (at an end of the optical fiber). The extent of this cone of radiation is defined by the numerical aperture of the optical fiber. It will be appreciated that rays of radiation which enter or leave the optical fiber at different angles will pass through different parts of the optical element. Rays which enter or leave the optical fiber at relatively small angles pass through a central portion of the optical element whereas rays which enter or leave the optical fiber at relatively large angles pass through an outer portion of the optical element.

It will be appreciated that since the optical element, the radiation system and the sensor system are generally co-axial and the radiation system and the sensor system are both disposed on the same side of the optical element, one of the radiation system and the sensor system (which may be referred to as the proximate system) is disposed between the optical element and the other one of the radiation system and the sensor system (which may be referred to as the distal system). The proximate system is arranged so as to provide radiation to, or receive radiation from, a central portion of the optical element. The proximate system will cause a central (since it is coaxial with the optical element) obscuration for the distal system such that the distal system cannot provide radiation to, or receive radiation from, a central portion of the optical element. However, the distal system is arranged so as to provide radiation to, or receive radiation from, an outer portion of the optical element. Therefore, the light that couples the proximate system to or from the optical element is generally from a different part of the angular distribution of light that couples the distal system to or from the optical element. Rays that enter or leave the optical fiber at relatively small angles couple to the proximate system whereas rays that enter or leave the optical fiber at relatively large angles couple to the distal system.

The apparatus according to the first aspect of the invention is advantageous for a number of reasons, as now discussed.

First, since the optical element, the radiation system and the sensor system are generally co-axial, the apparatus provides a compact arrangement for coupling into and out of the optical fiber. This is in contrast, for example, to an arrangement wherein the optical axes of the radiation system and the sensor system are generally mutually perpendicular and a beam splitter is used to couple both to the optical fiber.

Second, the apparatus according to the first aspect of the invention is beneficial over an arrangement wherein the optical axes of the radiation system and the sensor system are parallel but offset and wherein the radiation system and the sensor system are coupled to the optical element via a beam splitter, as now discussed. Again, the apparatus according to the first aspect of the invention provides a compact arrangement, especially in dimensions that are generally perpendicular to an optical axis of the optical fiber that the apparatus is arranged to couple into and out of.

Furthermore, for embodiments wherein the sensor system is operable to determine the colour of the output radiation, the input radiation may comprise white light and it may be desirable to minimize the amount of input radiation that is received by the sensor (so as to maximize the colour saturation). As discussed above, with an arrangement wherein the radiation system and the sensor system are generally co-axial, and both disposed on the same side of the optical element, the light that couples the radiation system to the optical element is generally from a different part of the angular distribution of light that couples the sensor system from the optical element. As a result, if the end of the optical fibre to which the apparatus is coupled is cut flat and square, all of the input radiation that reflects from the end will travel back to the radiation system rather than to the sensor system.

The sensor system may be disposed between the optical element and the radiation system such that the sensor system may be arranged to receive radiation from a central portion of the optical element.

This arrangement has a number of additional advantages, as now discussed.

The sensor system being arranged such that the output radiation received from the optical element comprises radiation received from a central portion of the optical element is advantageous for a number of reasons. First, the intensity of radiation exiting an optical fiber decreases as the angle with respect to the optical axis (at the end face of the optical fiber) increases. Furthermore, by selecting this central portion of the output radiation, dispersion effects are minimised since angular spread of the radiation that is received by the sensor system is minimised. This is particularly advantageous when the sensor system is arranged to determine spectral properties (for example colour hue) of the output radiation since such dispersive effects may affect such measurements.

It will be appreciated that some of the radiation produced by the radiation system may be blocked by the sensor system. However, even with a significant reduction in the amount of (white) light coupled into the optical fiber, the increase in the intensity of the output radiation achieved by the sensor system sampling a central portion of radiation output by the optical element, and the increase in the entrance aperture of the sensor system that this allows (for a given size of optical element) can still result in an overall efficiency increase.

The optical element may comprise a convex lens.

It will be appreciated that, alternatively, the optical element may comprise a mirror.

The radiation system may comprise a radiation source operable to produce the input radiation and radiation system optics arranged between the radiation source and the optical element.

The radiation system optics may be arranged to generally collimate the input radiation which is received by the optical element. For example, the radiation system optics may comprise a convex lens and the radiation source may be disposed at, or proximate to, a focal plane of said convex lens. The radiation source may be disposed at, or close to, an optical axis of the apparatus. The radiation system optics may be coaxial with the optical element.

The sensor system may comprise a sensor and sensor system optics arranged to focus the output radiation onto the sensor.

For example, the sensor system optics may comprise a convex lens and the sensor may be disposed at, or proximate to, a focal plane of said convex lens. The sensor may be disposed at, or close to, an optical axis of the apparatus. The sensor system optics may be coaxial with the optical element.

The at least one characteristic of the output radiation may comprise a colour of the output radiation.

The sensor may be a colour sensor integrated circuit.

The sensor may comprise a two-dimensional array of sensing elements such as, for example, photodiodes.

The apparatus may further comprise a support for the optical element, the radiation system and the sensor system.

The support may be formed from any suitable material such as, for example, a metal or a plastics material. The support may be of the form of a housing or the like, for example a three part housing. This support may aid in the relative positioning and alignment of the components of the apparatus.

The support may comprise an optical fiber connection portion.

The support may comprise one or more engagement features for one or more of: the optical element, the radiation system and the sensor system.

It will be appreciated that an engagement feature for the radiation system may comprise an engagement feature for a radiation source and/or radiation system optics (for example a lens).

It will be appreciated that an engagement feature for the radiation system may comprise an engagement feature for a radiation source and/or radiation system optics (for example a lens).

According to a second aspect of the invention there is provided a measurement device comprising: the apparatus according to the first aspect of the invention; a power supply; and a control unit, the control unit being operable to: control emission of radiation from the radiation system; receive a signal from the sensor system which is indicative of at least one characteristic of the output radiation received thereby to determine said at least one characteristic of the output radiation from the signal received from the sensor system.

The power supply may comprise a battery.

According to a third aspect of the invention there is provided a system for determining a property of a remote location, the system comprising: the measurement device according to the second aspect of the invention; and an optical fiber having a sensing distal end comprising a sensing material operable to change to a colour that is indicative of a chemical content of the environment to which it is exposed.

Various aspects and features of the invention set out above or below may be combined with various other aspects and features of the invention as will be readily apparent to the skilled person.

Embodiments of the invention will now be described, by way of example only, with reference to the accompanying schematic drawings, in which:

FIG. 1 is a side view of an apparatus for coupling radiation into and out of an optical fiber according to an embodiment of the present invention; and FIG. 2 is a cross sectional view of the apparatus for coupling radiation into and out of an optical fiber as shown in FIG. 1 through the line A-A;

Figure 3:
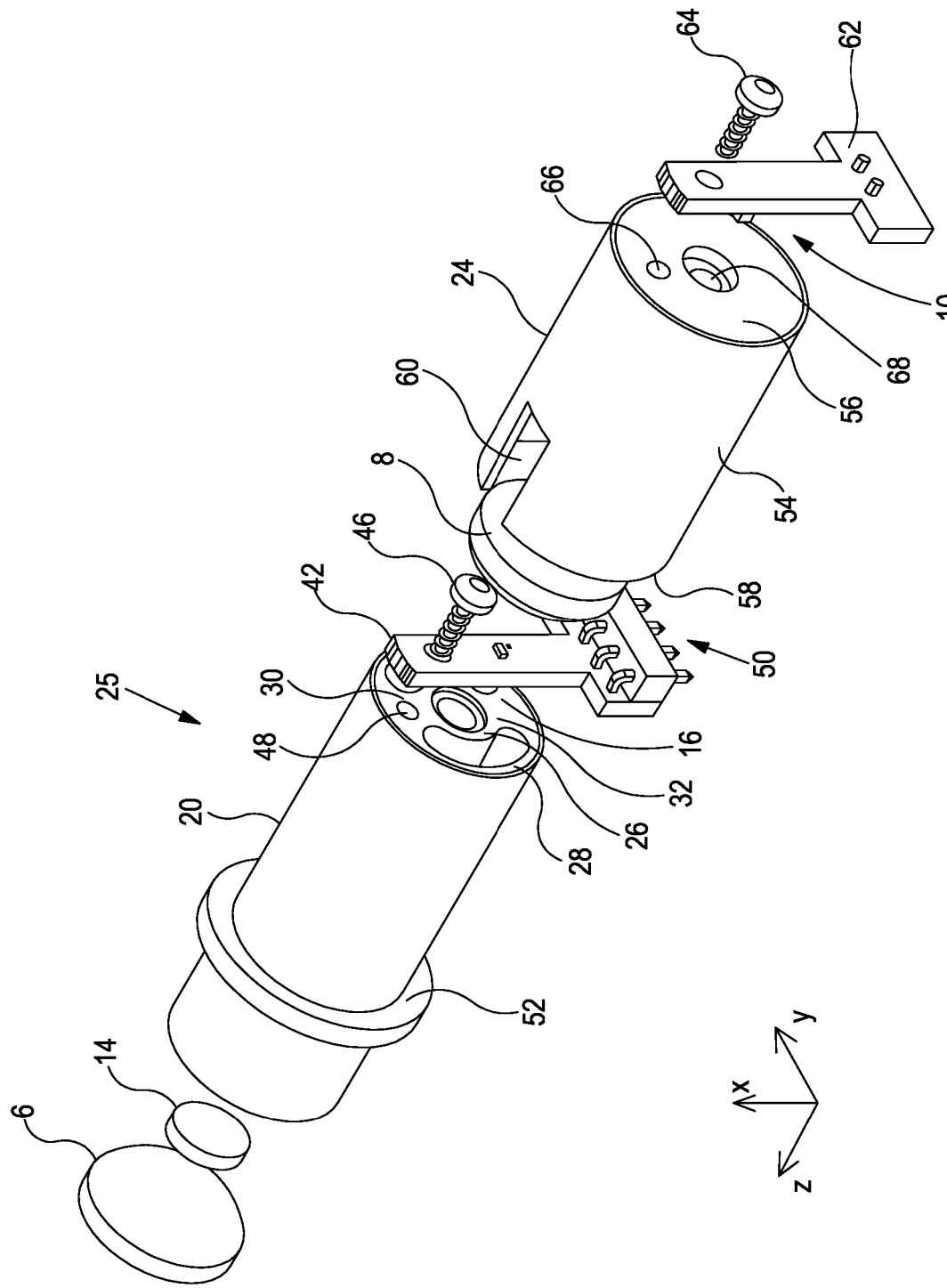
FIG. 3 is a perspective view of a sub-assembly that forms part of the apparatus as shown in FIGS. 1 and 2.

FIGS. 1 and 2 show an apparatus 2 for coupling radiation into and out of an optical fiber 4 according to an embodiment of the present invention. The apparatus 2 comprises a first lens 6 which may be considered to be an optical element for coupling radiation into and out of the optical fiber 4.

It will be appreciated that the dimensions and focal length of the first lens 6 may have a range of different values for different embodiments. In one embodiment, the first lens 6 may be a plano-convex lens having a diameter of 12.7 mm and a focal length of 15 mm.

The optical fiber 4 is dimensioned to be insertable into the lumen of a feeding tube. For example, the optical fiber may have a diameter of 0.7 mm.

The apparatus 2 further comprises a second lens 8 and a light source 10, which may be considered to be a radiation system. An axis of the second lens 8 may define an axis of the radiation system. The light source 10 is operable to produce light (which may be referred to as input radiation) and may be considered to be a radiation source that is operable to produce the input radiation. The second lens 8 is arranged between the light source 10 and the first lens 6 and may be considered to be radiation system optics. The light source 10 is disposed at, or close to, an optical axis 12 of the apparatus 2. It will be appreciated that the light source 10 may act substantially as a point source and will produce input radiation that propagates in a range of angles away from the light source 10. At least part of this input radiation is received by the second lens 8.

The second lens 8 is arranged to generally collimate this input radiation which, as will be described further below, is partially received by the first lens 6. In order to achieve this, the light source 10 is disposed at, or proximate to, a focal plane of the second lens 8. It will be appreciated that the dimensions and focal length of the second lens 8 may have a range of different values for different embodiments. In one embodiment, the second lens 8 may be a plano-convex lens having a diameter of 12.7 mm and a focal length of 15 mm.

Therefore the radiation system (comprising the second lens 8 and the light source 10) may be considered to be operable to produce input radiation, the radiation system being arranged such that the input radiation is at least partially received by the first lens 6.

The light source 10 may, for example, illuminate the sensing distal end with white light with a wavelength in the range of 405 nm to 685 nm. The light source 10 may, for example, comprise a light emitting diode.

The apparatus 2 further comprises a third lens 14 and a sensor 16, which may be considered to be a sensor system. An axis of the third lens 14 may define an axis of the sensor system. The third lens 14 is arranged between the sensor 16 and the first lens 6 and may be considered to be sensor system optics. The sensor 16 is disposed at, or close to, the optical axis 12 of the apparatus 2. As will be described further below, the third lens 14 is arranged to focus output radiation received from a central portion of the first lens 6 onto the sensor 16. In order to achieve this, the sensor 16 may be disposed at, or proximate to, a focal plane of the third lens 14.

It will be appreciated that the dimensions and focal length of the third lens 14 may have a range of different values for different embodiments. In one embodiment, the third lens 14 may be a plano-convex lens having a diameter of 6 mm and a focal length of 30 mm. It will be appreciated that the focal length of the third lens 14 may be larger, for example by a factor of 2, than the focal length of the first lens 6. Therefore, the image of the distal end of the optical fiber 4 which is formed on the sensor 16 may be larger (for example by a factor of two) than the distal end of the optical fiber 4. In one embodiment, the optical fiber has a diameter of 0.7 mm and the image of the distal end of the optical fiber 4 which is formed on the sensor 16 has a diameter of 1.4 mm. This will comfortably overfill the sensor 16.

The first, second and third lenses 6, 8, 14 are co-axial and define the axis 12 of the apparatus 2.

The sensor 16 is suitable for receiving output radiation from the first lens 6 and is operable to determine at least one characteristic of the output radiation, or to output a signal indicative of said at least one characteristic of the output radiation. The at least one characteristic of the output radiation may comprise a colour of the output radiation.

The sensor 16 may comprise a colour sensor integrated circuit. The sensor 16 may comprise a two-dimensional array of sensing elements such as, for example, photodiodes. The sensor 16 may be a Red-Green-Blue, RGB, detector. The sensor 16 may be operable to determine an intensity of red, green and blue components of the output radiation. The sensor 16 may have a generally square active sensing area with dimensions of the order of 0.4 mm×0.4 mm.

The apparatus 2 further comprises a support 18 for: the first lens 6; the second lens 8 and the light source 10 (which form the radiation system); and the third lens 14 and the sensor 16 (which form the sensor system). The support 18 is of the form of a three part housing, comprising: a central body 20, a first end body 22 and a second end body 24. The central body 20 supports the first lens 6, the third lens 14 and the sensor 16. The first end body 22 defines an optical fiber connection portion, as discussed further below. The second end body 24 supports the second lens 8 and the light source 10.

Each of the central body 20, the first end body 22 and the second end body 24 may be formed from any suitable material such as, for example, a metal or a plastics material. The support 18 (which comprises the central body 20, the first end body 22 and the second end body 24) aids in the relative positioning and alignment of the components of the apparatus, as described below.

The central body 20 and the second end body 24 are now described in further detail with reference to FIGS. 3 to 7. In FIGS. 1 to 7, a consistent set of right-handed Cartesian axes are used, wherein the optical axis 12 of the apparatus 2 extends in the z-direction. In the following, unless stated to the contrary, it will be appreciated that axial refers to a direction that is parallel to the optical axis 12 (i.e. in the z-direction) and radial refers to a direction that is perpendicular to the optical axis 12 and passes through it.

Figure 4:
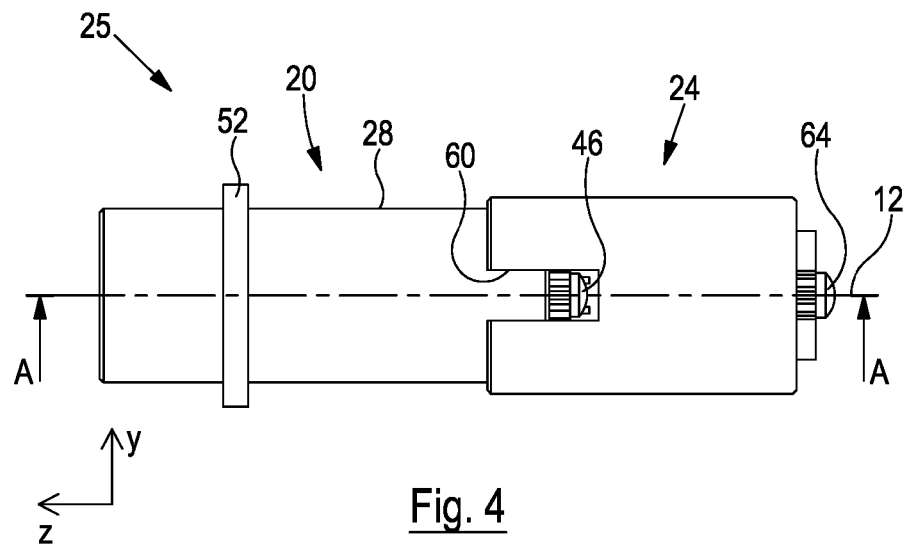
FIG. 4 is a side view of the sub-assembly shown in FIG. 3.
Figure 5:
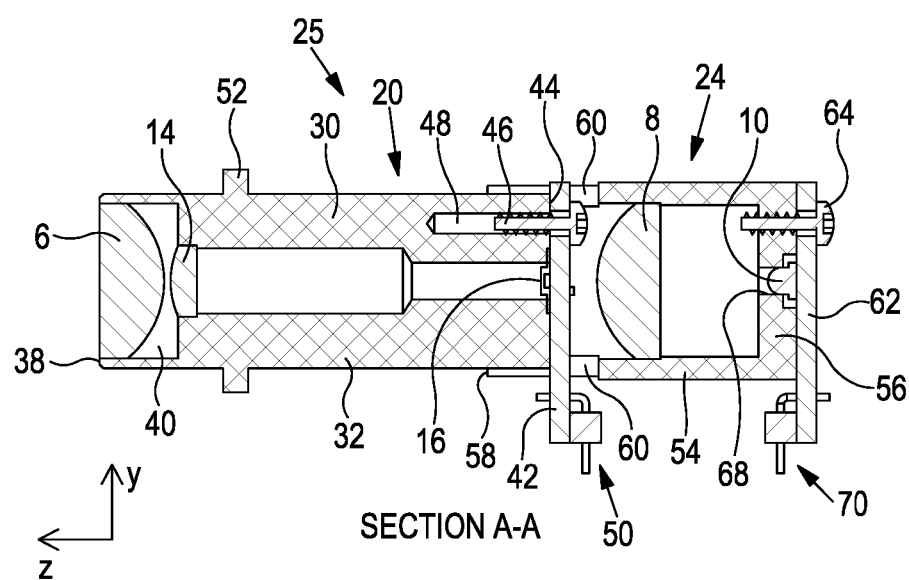
FIG. 5 is a cross sectional view of the sub-assembly shown in FIGS. 3 and 4 through the line A-A (see FIG. 4)

FIGS. 3 to 5 show a sub-assembly 25 of the apparatus 2 shown in FIGS. 1 and 2. The sub-assembly 25 may be considered to be an apparatus for coupling radiation into and out of an optical fiber according to an embodiment of the present invention. The sub-assembly 25 of the apparatus 2 shown in FIGS. 1 and 2 comprises all of the components of the apparatus 2 with the exception of the first end body 22.

The central body 20 is generally cylindrical and, in particular comprises mutually coaxial inner and outer tubular portions 26, 28. The inner and outer tubular portions 26, 28 are connected via two diametrically opposed web portions 30, 32 which extend generally radially between the inner and outer tubular portions 26, 28. The two web portions 30, 32 divide a space between the coaxial inner and outer tubular portions 26, 28 into two axially extending arcuate apertures 34, 36. It will be appreciated that in the cross section shown in FIG. 5 (which is in the x-z plane) the two web portions 30, 32 can be seen whereas the arcuate apertures 34, 36 cannot and that the cross sections shown in FIGS. 2 and 6 (which are in the y-z plane) the arcuate apertures 34, 36 can be seen whereas the two web portions 30, 32 cannot.

As can be seen in FIGS. 2 and 4, the outer tubular portion 28 of the central body 20 extends axially further than the inner tubular portion 26 (and the two web portions 30, 32) at a first end 38 of the central body 20 so as to form a recess 40.

The third lens 14 is received in an end portion of the inner tubular portion 26 proximate the first end 38 of the central body 20. The third lens 14 may be push fit into the end of the inner tubular portion 26. An inner surface of the inner tubular portion 26 may be stepped. In particular, the inner tubular portion 26 may comprise a counter bore that forms a shoulder against which the third lens 14 can abut. This shoulder forms a convenient location feature for the third lens 14 and aids in the accurate placement of the third lens 14. The third lens 14 may be press fit into the inner tubular portion 26. Optionally, in some embodiments the third lens 14 may be held in place using a suitable adhesive.

The first lens 6 is received in an end portion of the outer tubular portion 28 proximate the first end 38 of the central body 20. It will be appreciated that the first lens 6 is received in the recess 40 at the first end 38 of the outer tubular portion 28 formed by the greater axial extent of the outer tubular portion 28. The first lens 6 may be push fit into the end of the outer tubular portion 28. An inner surface of the outer tubular portion 28 may be stepped. In particular, the outer tubular portion 28 may comprise a counter bore that forms a shoulder against which the first lens 6 can abut. This shoulder forms a convenient location feature for the first lens 6 and aids in the accurate placement of the first lens 6. The first lens 6 may be press fit into the outer tubular portion 28. Optionally, in some embodiments the first lens 6 may be held in place using a suitable adhesive.

As can be best seen in FIGS. 3 and 4, the sensor 16 is provided on a generally T-shaped sensor printed circuit board (sensor PCB) 42. The sensor PCB 42 is connected to a second end 44 of the central body 20 using a screw 46 that engages with a bore 48 formed in one of the web portions 30. The sensor 16 is received in an end portion of the inner tubular portion 26 proximate the second end 44 of the central body 20. The inner tubular portion 26 may comprise a counter bore that forms a shoulder against which a generally circular support for the sensor 16 can abut. This shoulder forms a convenient location feature for the sensor 16 and can aid in accurate placement of the sensor 16 on the optical axis 12. It will be appreciated that the sensor PCB 42 is provided with connecting leads 50 or the like to allow signals to be exchanged between the sensor 16 and other parts of the apparatus 2.

On an outer surface of the outer tubular portion 28, central body 20 is provided with a generally annular flange 52 that extends around the circumference of the central body 20. As described further below, this flange 52 can provide a location feature for the central body 20 for mounting the central body 20 within a housing.

The second end body 24 is generally of the form of a cylindrical cap, comprising a curved cylinder wall 54 and an end wall 56. The end wall 56 defines a first end of the second end body 24. An inner surface of the curved cylinder wall 54 is stepped so as to form two generally annular shoulders, as now described.

A second end 58 of the second end body 24 is open and is provided with a counter bore (or a portion of the bore with a greater internal radius) for receipt of a portion of the central body 20 proximate its second end 44. The counter bore forms a shoulder (not shown) against which the second end 44 of the central body 20 can abut. The curved wall 54 is provided with two diametrically opposed, axially extending recesses 60 for receipt of part of the sensor PCB 42 to allow insertion of the second end 44 of the central body 20 into the second end 58 of the second end body 24.

Intermediate the counter bore that receives a portion of the central body 20 proximate its second end 44 and a main portion of the curved cylinder wall 54 there is formed an intermediate bore portion having an internal radius that is intermediate that of said counter bore and said main portion. The second lens 8 is received in this intermediate bore portion. The intermediate bore portion forms a shoulder against which the second lens 8 can abut.

As can be best seen in FIGS. 3 and 4, the light source 10 is provided on a generally T-shaped radiation source printed circuit board (radiation source PCB) 62. The radiation source PCB 62 is connected to the end wall 56 of the second end body 24 using a screw 64 that engages with a bore 66 formed in the end wall 56. The generally circular end wall 56 is provided with a central through aperture 68. The light source 10 is received in said through aperture 68. The through aperture 68 may comprise a counter bore that forms a shoulder against which a generally circular support for the light source 10 can abut. This shoulder forms a convenient location feature for the light source 10 and can aid in accurate placement of the light source 10 on the optical axis 12. It will be appreciated that the radiation source PCB 62 is provided with connecting leads 70 or the like to allow signals to be exchanged between the light source 10 and other parts of the apparatus 2.

As can be seen in FIG. 2, the first end body 22 is generally of the form of a stepped tube, comprising mutually-coaxial, first and second generally cylindrical portions 72, 74.

The first generally cylindrical portion 72 is open and is provided with a counter bore (or a portion of the bore with a greater internal radius) for receipt of a portion of the central body 20 proximate its first end 38. The counter bore forms a shoulder against which the first end 38 of the central body 20 can abut and aids in the accurate placement of the central body 20 relatibe the to the first end body 22.

The second generally cylindrical portion 74 is open and is for receipt of a connector 76 provided at an end of the optical fiber 4. The connector 76 is generally cylindrical and is a push fit into the second generally cylindrical portion 74. The connector 76 is provided on an external surface thereof with a generally annular flange 78 that abuts an end of the second generally cylindrical portion 74.

The sub-assembly 25 shown in FIGS. 3 to 5 and described above may form part of a measurement device, as now discussed with reference to FIG. 8.

Figure 8:
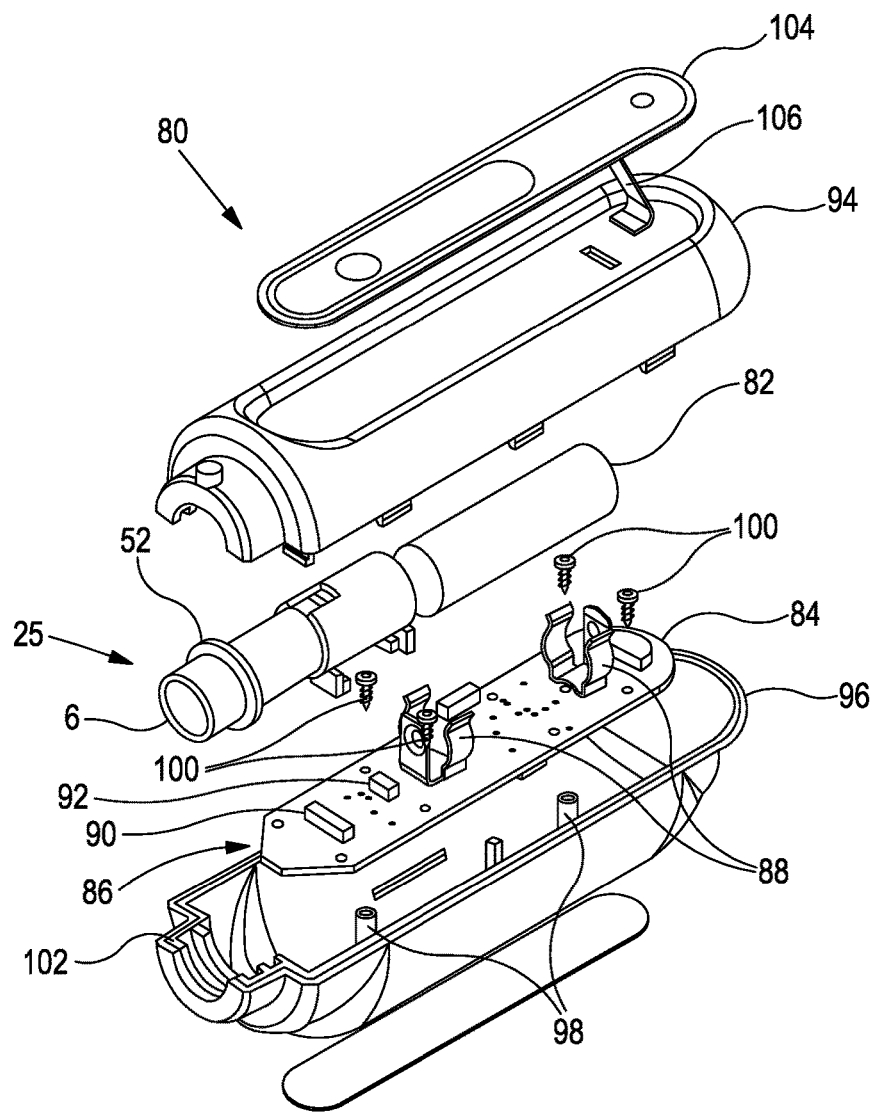
FIG. 8 is an exploded perspective view of a measurement device comprising the sub-assembly shown in FIGS. 3 to 5.
Figure 9:
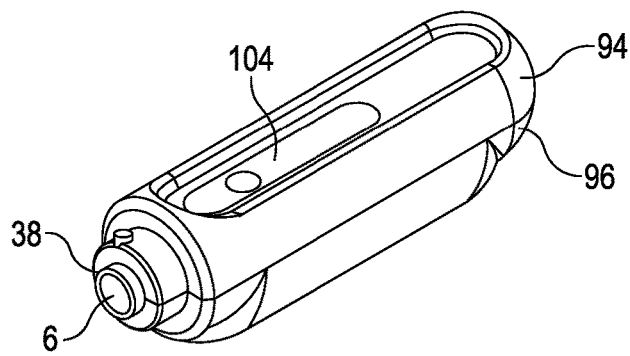
FIG. 9 is a perspective view of the measurement device shown in FIG. 8.

FIG. 8 shows a measurement device 80 according to an embodiment of the present invention. The measurement device 80 comprises the sub-assembly 25 shown in FIGS. 3 to 5, a battery 82 and a control unit 84. The control unit 84 is operable to control emission of radiation from the light source 10, via a control signal or the like. The control unit 84 is further operable to receive a signal from the sensor 16 which is indicative of at least one characteristic of the output radiation received thereby. The control unit 84 is further operable to determine said at least one characteristic of the output radiation from the signal received from the sensor 16. The control unit 84 may comprise any suitable processor or microprocessor, as will be understood by the skilled person.

The control unit 84 is provided on a main printed circuit board (main PCB) 86. The main PCB 86 supports the sub-assembly 25 and the battery 82. For this purpose, the main PCB 86 is provided with: battery connectors 88; a connector 90 for connection to the connecting leads 50 of the sensor PCB 42; and a connector 92 for connection to the connecting leads 70 of the radiation source PCB 62. The battery connectors 88 are arranged to support the battery 82 (which may be an AA battery) and also provide electrical connections to the battery to allow the battery 82 to provide power to other parts of the measurement device 80. The connectors 90, 92 for connection to the connecting leads 50, 70 of the sensor PCB 42 and the radiation source PCB 62 are arranged to support the sub-assembly 25. The sensor 16 is operable to send a signal which is indicative of at least one characteristic of the output radiation received thereby to the control unit 84 via the connecting lead 50 and the connector 90. The control unit 84 is operable to send a control signal to the light source 10 via the connector 92 and the connecting leads 70.

The measurement device 80 further comprises a first housing member 94 and a second housing member 96. The first and second housing members 94, 96 are arranged to engage, via a snap-fit engagement or the like, so as to form a generally cylindrical housing for the sub-assembly 25, the battery 82 and the control unit 84.

The second housing member 96 is provided on an internal surface thereof with a plurality of hollow bosses 98. The main PCB 86 is attached to the second housing member 96 via a plurality of screws 100, which engage with the hollow bosses 98.

The housing formed by the first and second housing members 94, 96 defines an aperture through which a portion of the central body 20 proximate its first end 38 extends.

Each of the first and second housing members 94, 96 is provided with a portion that forms part of a cylindrical protrusion of the housing surrounding the aperture through which a portion of the central body 20 proximate its first end 38 extends. On an internal surface of this protrusion is formed a groove 102 for receipt of the generally annular flange 52 that is provided on the outer surface of the outer tubular portion 28. This provides a location feature for accurate placement of the sub-assembly 25 within the housing and provides support for the sub-assembly 25.

The measurement device 80 further comprises a user interface 104. It will be appreciated that the user interface 104 may comprise display means for displaying information to a user and input means for a user to provide an input signal. The display means may comprise one or more light emitting diodes. The input means may comprise one or more buttons or the like. The user interface 104 is provided with a connector lead 106 which provides communication between the user interface 104 and the control unit 84.

In use, the measuring device 80 can be used as follows.

First an optical fiber 4 is provided with a connector 76 and a first end body 22. The connector 76 is push fit into the second generally cylindrical portion 74 of the first end body 22. The first generally cylindrical portion 72 of the first end body 22 is engaged a portion of the central body 20 proximate its first end 38, which extends from the housing 94, 96.

The optical fiber 4 is dimensioned to be insertable into the lumen of a feeding tube, the optical fiber having a sensing distal end comprising a sensing material operable to change to a colour that is indicative of a chemical content of the environment to which it is exposed. The sensing material may be operable to change to a colour upon exposure of the sensing distal end to an environment having a pH of 5.5 or less. Alternatively, or additionally, the sensing material may be operable to change to a colour upon exposure of the sensing distal end to an environment having a pH of 4 or less. The sensing material may comprise one or more of: Thymol Blue, Methyl Red, Bromothymol Blue, Phenolphthalein, Bromocresol green, Fluorescein, Ether, or Universal Indicator. Other suitable indicators will become apparent to the skilled person on reading the present disclosure depending on the particular environment (i.e. physical or chemical environment) which is deemed to be indicative of the desired final location of the feeding tube. The chemical or biological indicator may change colour or other optical characteristic depending on the presence of specific predetermined markers such as, for example, pH level or Biological Markers such as Human Gastric Lipase, Pepsin, Intrinsic Factor, Mucin and Gastrin.

The user interface 104 may be used to actuate the measuring device 80 by pressing a button or the like. This may send an actuation signal to the control unit 84. In turn, the control unit 84 may generate a control signal that is sent to the light source 10 to cause it to emit radiation. The control unit 84 may, for example, be operable to enable the light source 10 to emit a pulse of input radiation. For example, the pulse of input radiation may be in the range of 6 to 10 milliseconds. For example, the pulse of input radiation may be of 8 milliseconds duration.

At least a portion of the pulse of input radiation is incident on the second lens 8 which, as explained above, is arranged to generally collimate this input radiation. A portion of the collimated input radiation passes through the two axially extending arcuate apertures 34, 36 and is received by the first lens 6. The first lens 6 is arranged to focus this portion of the input light at, or proximate to, an end of the optical fiber 4. In order to achieve this, engagement between the optical fiber 4, the connector 76, the first end body 22 and the first end body 22 is such that the end of the optical fiber 4 is disposed at, or proximate to, a focal plane of the first lens 6. This input light propagates along the optical fiber and illuminates the sensing distal end thereof.

The light source 10 may, for example, illuminate the sensing distal end with white light with a wavelength in the range of 405 nm to 685 nm.

A portion of the input radiation is reflected by the sensing material at the sensing distal end. The colour of the reflected radiation (which may be referred to as output radiation) is dependent on the colour of the sensing material.

The output radiation is output at a proximal end of the optical fiber 4. It will be appreciated that, since the end of the optical fiber 4 may be disposed at, or proximate to, a focal plane of the first lens 6, the first lens may act to collimate the output radiation.

The third lens 14 is arranged to focus a portion of this output radiation, which is received from a central portion of the first lens 6, onto the sensor 16. In order to achieve this, the sensor 16 may be disposed at, or proximate to, a focal plane of the third lens 14.

The sensor 16 may be operable to generate one or more signals indicative of one or more characteristics of the output radiation (for example its colour or hue). These signals are communicated to the control unit 84, which is operable, from these signals, to determine the one or more characteristics of the output radiation.

The first, second and third lenses 6, 8, 14 are co-axial and define the axis 12 of the apparatus 2. It will be appreciated that an axis of the second lens 8 may define an axis of the radiation system and that an axis of the third lens 14 may define an axis of the sensor system. Therefore, the first lens 6, the radiation system (formed by second lens 8 and light source 10) and the sensor system (formed by third lens 14 and sensor 16) are generally co-axial. The radiation system and the sensor system are both disposed on the same side of the first lens 6.

The apparatus 2 (and, in particular, the sub-assembly 25) provides an arrangement that is operable to couple radiation into and out of an optical fiber 4.

It will be appreciated that, in general, radiation may enter and/or leave an optical fiber 4 at a range of different angles to an optical axis of the optical fiber (at an end of the optical fiber). The extent of this cone of radiation is defined by the numerical aperture of the optical fiber 4. It will be appreciated that rays of radiation which enter or leave the optical fiber 4 at different angles to this axis will pass through different parts of the first lens 6. Rays which enter or leave the optical fiber at relatively small angles pass through a central portion of the first lens 6 whereas rays which enter or leave the optical fiber at relatively large angles pass through an outer portion of the first lens 6.

It will be appreciated that since the first lens 6, the radiation system and the sensor system are generally co-axial and the radiation system and the sensor system are both disposed on the same side of the first lens 6, one of the radiation system and the sensor system (which may be referred to as the proximate system) is disposed between the first lens 6 and the other one of the radiation system and the sensor system (which may be referred to as the distal system). In particular, in the above-described embodiments, the sensor system is disposed between the first lens 6 and the radiation system such that the sensor system is arranged to receive radiation from a central portion of the first lens 6. Therefore, in this embodiment, the sensor system may be referred to as the proximate system and the radiation system may be referred to as the distal system.

The sensor system is arranged so as to receive radiation from a central portion of the first lens 6. The sensor system causes a central obscuration for the radiation system such that the radiation system cannot provide radiation to a central portion of the first lens 6. However, the radiation system is arranged so as to provide radiation to an outer portion of the first lens 6. Therefore, the light that couples the sensor system to or from the first lens 6 is generally from a different part of the angular distribution of light that couples the radiation system to or from the first lens 6. Rays that enter or leave the optical fiber at relatively small angles couple to the sensor system whereas rays that enter or leave the optical fiber at relatively large angles couple to the radiation system.

The apparatus 2 according to the first aspect of the invention is advantageous for a number of reasons, as now discussed.

First, since the first lens 6, the radiation system and the sensor system are generally co-axial, the apparatus 2 provides a compact arrangement for coupling into and out of the optical fiber. This is in contrast, for example, to an arrangement wherein the optical axes of the radiation system and the sensor system are generally mutually perpendicular and a beam splitter is used to couple both to the optical fiber 4.

Second, the apparatus 2 is beneficial over an arrangement wherein the optical axes of the radiation system and the sensor system are parallel but offset and wherein the radiation system and the sensor system are coupled to the optical element via a beam splitter, as now discussed. Again, the apparatus 2 provides a compact arrangement, especially in dimensions that are generally perpendicular to an optical axis of the optical fiber 4 that the apparatus 2 is arranged to couple into and out of.

Furthermore, for embodiments wherein the sensor system is operable to determine the colour of the output radiation, the input radiation may comprise white light and it may be desirable to minimize the amount of input radiation that is received by the sensor 16 (so as to maximize the colour saturation). As discussed above, with an arrangement wherein the radiation system and the sensor system are generally co-axial, and both disposed on the same side of the optical element, the light that couples the radiation system to the optical element is generally from a different part of the angular distribution of light that couples the sensor system from the optical element. As a result, if the end of the optical fibre 4 to which the apparatus 2 is coupled is cut flat and square, all of the input radiation that reflects from the end of the optical fiber 4 will travel back to the radiation system rather than to the sensor system.

The sensor system being arranged such that the output radiation received by the sensor 16 from the first lens 6 comprises radiation received from a central portion of the first lens 6 is advantageous for a number of reasons. First, the intensity of radiation exiting an optical fiber decreases as the angle with respect to the optical axis (at the end face of the optical fiber) increases. Furthermore, by selecting this central portion of the output radiation, dispersion effects are minimised since the angular spread of the radiation that is received by the sensor system is minimised. This is particularly advantageous when the sensor system is arranged to determine spectral properties (for example colour hue) of the output radiation since such dispersive effects may affect such measurements.

It will be appreciated that some of the radiation produced by the radiation system may be blocked by the sensor system. However, even with a significant reduction in the amount of (white) light coupled into the optical fiber 4, the increase in the intensity of the output radiation achieved by the sensor system sampling a central portion of radiation output by the optical element, and the increase in the entrance aperture of the sensor system that this allows (for a given size of optical element) can still result in an overall efficiency increase.

Figure 7:
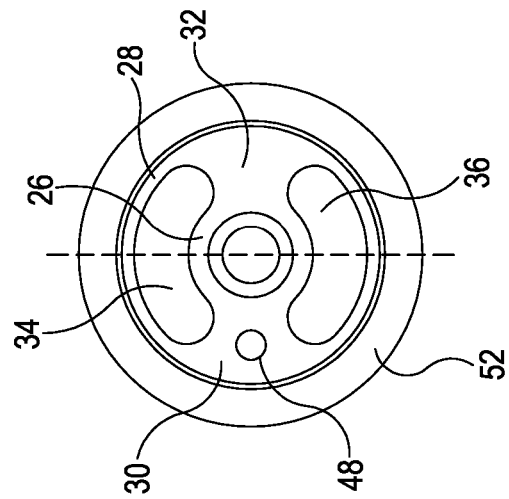
FIG. 7 is an end view of the central housing shown in FIG. 6.
Figure 6:
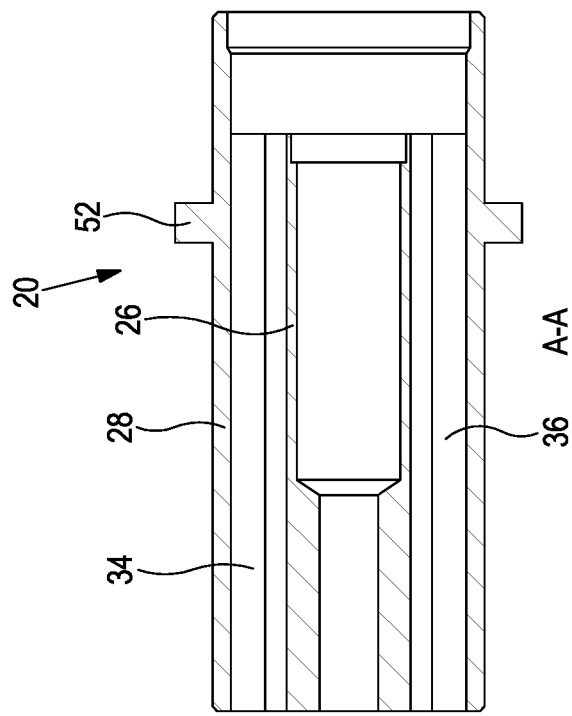
FIG. 6 is a cross sectional view of a central housing that forms part of the sub-assembly shown in FIGS. 3 to 5.
Figure 10:
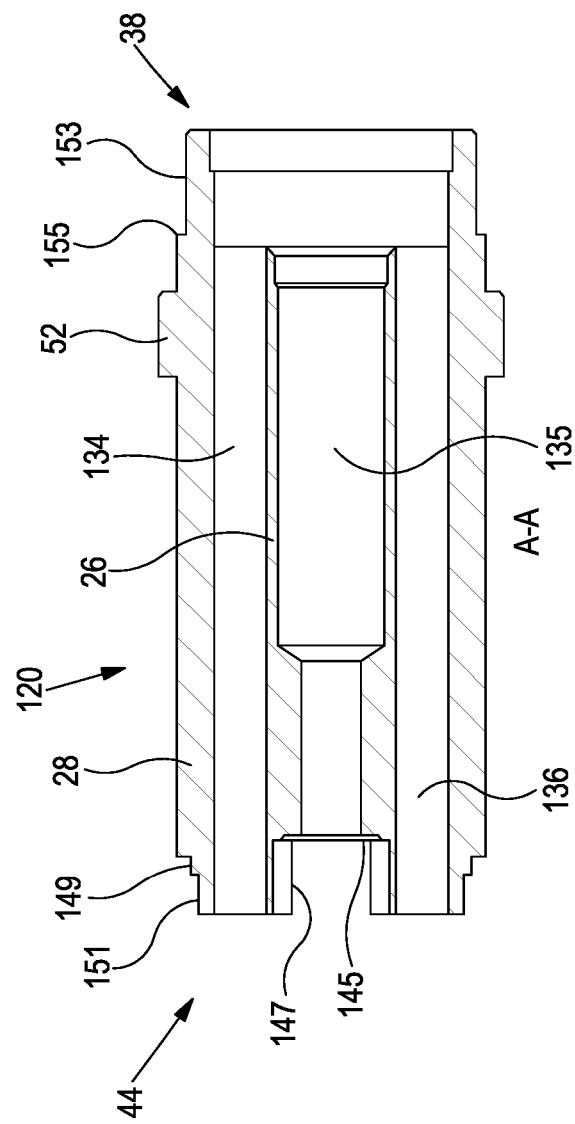
FIG. 10 is a cross sectional view of another embodiment of a central housing that could replace the central housing shown in FIGS. 6 and 7 in the sub-assembly shown in FIGS. 3 to 5.
Figure 11:
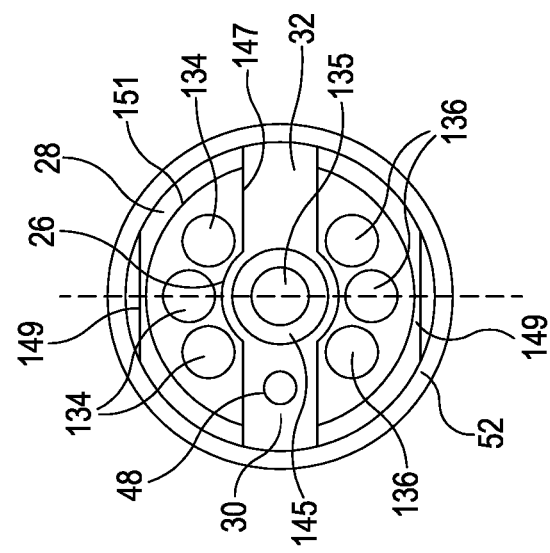
FIG. 11 is an end view of the central housing shown in FIG. 10.

Another embodiment of a central housing 120 that could replace the above-described central housing 20 shown in FIGS. 6 and 7 is now described with reference to FIGS. 10 and 11. FIG. 10 is a cross sectional view the central housing 120 and FIG. 11 is an end view of the central housing 120. It will be appreciated that the central housing 120 has may features in common with the central housing 20 shown in FIGS. 6 and 7. Only the differences will be described in detail below and it will be appreciated that any features that are generally the same in the two embodiments (and only differ in minor detail) share common reference numerals in the two embodiments.

The central body 120 is generally cylindrical. As with the central housing 20 in FIGS. 6 and 7, the central body 120 is hollow, having a central bore 135 extending there-through. Each of the two axially extending arcuate apertures 34, 36 of the central body 20 in FIGS. 6 and 7 have been replaced with three axially extending circular cross-section bores 134, 136 respectively. The circular cross-section bores 134, 136 can still be considered to divide the central housing 120 into mutually coaxial inner and outer tubular portions 26, 28. The inner tubular portion 26 may be considered to be the portion of the central housing that is radially inboard of the circular cross-section bores 134, 136 and the outer tubular portion 28 may be considered to be the portion of the central housing that is radially outboard of the circular cross-section bores 134, 136. A first set of the circular cross-section bores 134 (which general replaces a first one of the arcuate apertures 34) is separated from a second set of the circular cross-section bores 136 (which general replaces a second one of the arcuate apertures 36) by two diametrically opposed web portions 30, 32 which extend generally radially between the inner and outer tubular portions 26, 28.

It will be appreciated that in addition to the two web portions 30, 32 (which occupy a space that in use coincide with an obscuration provided by the sensor PCB 42) additional connections are formed between the inner and outer tubular portions 26, 28 by material provided between adjacent circular-cross section apertures 134, 136.

In a similar manner to the embodiment shown in FIGS. 6 and 7, in use, at least a portion of the input radiation output by the radiation system is collimated by the second lens 8 and then propagates through the axially extending apertures 134, 136 to the first lens 6.

This arrangement whereby the light path for the radiation from the radiation system to the first lens 6 comprises a plurality of circular cross-section apertures may be more convenient from a manufacturing perspective. For example, this circular aperture shape may be particularly suitable for manufacturing processes such as computer numerical control (CNC) machining processes. The circular cross-section apertures 134, 136 can be drilled in-situ on a CNC lathe and may be more easily formed than the arcuate apertures 34, 36 of the embodiment shown in FIGS. 6 and 7. Furthermore, any reduction in the amount of radiation reaching the first lens 6 may be insignificant.

As with the embodiment shown in FIGS. 6 and 7, in use, the sensor 16 is received in an end portion of the inner tubular portion 26 proximate the second end 44 of the central body 120. Also as with the embodiment shown in FIGS. 6 and 7, the inner tubular portion 26 comprises a counter bore that forms an annular shoulder 145 against which a generally circular support for the sensor 16 can abut. This shoulder 145 forms a convenient location feature for the sensor 16 and can aid in accurate placement of the sensor 16 on the optical axis 12. In addition, in this embodiment, a radially extending slot 147, or notch, is formed on the second end 44 of the central body 120, the counter bore that forms an annular shoulder 145 being formed in said slot 147. The slot 147 extends generally across the second end 44 of the central body 120 and is dimensioned so as to receive the sensor PCB 42. Again, the slot 147 may form an assembly and/or alignment feature for the sensor PCB 42, aiding assembly of the apparatus 2. It may also act to constrain the sensor PCB 42, reducing movement thereof. Again, a bore 48 formed in one of the web portions 30 to aid connection of the sensor PCB 42 to the second end 44 of the central body 120 using a screw 46.

In addition, at the second end 44 of the central body 120, an external surface of the outer tubular portion 28 is provided with some features which may aid location and assembly with the second end body 24. In particular, at the second end 44, the outer tubular portion 28 of the central body 120 is stepped so as to provide a smaller diameter portion 151 that may, in use, at least partially be received within the second end body 24. In addition, a main (larger diameter) part of the outer tubular portion 28 is provided with two diametrically opposed flat portions 149. These flat portions 149 may engage with complementary features on an interior of the second end body 24 to provide alignment and/or assembly features. Additionally or alternatively, a step formed between the smaller diameter portion 151 and a main (larger diameter) part of the outer tubular portion 28 may engage with a complementary feature on an interior of the second end body 24 to provide alignment and/or assembly features.

In addition, at the first end 38 of the central body 120, an external surface of the outer tubular portion 28 is provided with a feature which may aid location and assembly with the first end body 22. In particular, at the first end 38, the outer tubular portion 28 of the central body 120 is stepped so as to provide a smaller diameter portion 153 that may, in use, at least partially be received within the first end body 22. A step 155 formed between the smaller diameter portion 153 and a main (larger diameter) part of the outer tubular portion 28 may engage with a complementary feature on an interior of the first end body 22 to provide alignment and/or assembly features.

While specific embodiments of the invention have been described above, it will be appreciated that the invention may be practiced otherwise than as described. The descriptions above are intended to be illustrative, not limiting. Thus it will be apparent to one skilled in the art that modifications may be made to the invention as described without departing from the scope of the claims set out below.

The invention claimed is:

1. An apparatus for coupling radiation into and out of an optical fiber, the apparatus comprising:
   an optical element for coupling radiation into and out of the optical fiber;
   a radiation system operable to produce input radiation, the radiation system arranged so that the input radiation is at least partially received by the optical element; and
   a sensor system for receiving output radiation from the optical element and operable to generate a signal indicative of at least one characteristic of the output radiation, wherein the sensor system comprises a sensor and sensor optics arranged to focus the output radiation onto the sensor, the sensor being a color sensor integrated circuit;

wherein the optical element, the radiation system and the sensor system are substantially co-axial and the radiation system and the sensor system are both disposed on the same side of the optical element.

2. The apparatus of claim 1, wherein the sensor system is disposed between the optical element and the radiation system so that the sensor system receives radiation from a central portion of the optical element.

3. The apparatus of claim 1, wherein the optical element comprises a convex lens.

4. The apparatus of claim 1, wherein the radiation system comprises a radiation source operable to produce the input radiation and radiation system optics arranged between the radiation source and the optical element.

5. The apparatus of claim 1, wherein the sensor comprises a two-dimensional array of sensing elements.

6. The apparatus of claim 1, further comprising a support for the optical element, the radiation system and the sensor system.

7. The apparatus of claim 6, wherein the support comprises an optical fiber connection portion.

8. The apparatus of claim 6, wherein the support comprises one or more engagement features for one or more of: the optical element, the radiation system and the sensor system.

9. A measurement device comprising:
an apparatus for coupling radiation into and out of an optical fiber, comprising:
an optical element for coupling radiation into and out of the optical fiber;
a radiation system operable to produce input radiation, the radiation system arranged so that the input radiation is at least partially received by the optical element; and
a sensor system for receiving output radiation from the optical element and operable to generate a signal indicative of at least one characteristic of the output radiation, wherein the sensor system comprises a sensor and sensor optics arranged to focus the output radiation onto the sensor, the sensor being a color sensor integrated circuit,
wherein the optical element, the radiation system and the sensor system are substantially co-axial and the radiation system and the sensor system are both disposed on the same side of the optical element,
a power supply; and
a control unit, the control unit being operable to:
control emission of radiation from the radiation system; and
receive a signal from the sensor system which is indicative of at least one characteristic of the output radiation received to thereby determine said at least one characteristic of the output radiation from the signal received from the sensor system.

10. A system for determining a property of a remote location, the system comprising:
a measurement device comprising:
an apparatus for coupling radiation into and out of an optical fiber, comprising:
an optical element for coupling radiation into and out of the optical fiber;
a radiation system operable to produce input radiation, the radiation system arranged so that the input radiation is at least partially received by the optical element; and
a sensor system for receiving output radiation from the optical element and operable to generate a signal indicative of at least one characteristic of the output radiation, wherein the sensor system comprises a sensor and sensor optics arranged to focus the output radiation onto the sensor, the sensor being a color sensor integrated circuit,
wherein the optical element, the radiation system and the sensor system are substantially co-axial and the radiation system and the sensor system are both disposed on the same side of the optical element,
a power supply; and
a control unit, the control unit being operable to:
control emission of radiation from the radiation system; and
receive a signal from the sensor system which is indicative of at least one characteristic of the output radiation received to thereby determine said at least one characteristic of the output radiation from the signal received from the sensor system;
and
an optical fiber having a sensing distal end comprising a sensing material operable to change to a color that is indicative of a chemical content of an environment to which it is exposed.

11. The apparatus of claim 5, wherein the two-dimensional array of sensing elements are photodiodes.

* * * * *